United States Patent

Inoue et al.

[11] Patent Number: 5,338,869
[45] Date of Patent: Aug. 16, 1994

[54] HYDROXYPHENYLPROPIONIC ESTER HAVING NOVEL CRYSTAL STRUCTURE

[75] Inventors: Kikumitsu Inoue; Manji Sasaki, both of Nishinomiya; Shinichi Yachigo, Toyonaka, all of Japan

[73] Assignee: Sumitomo Chemical Company, Limited, Osaka, Japan

[21] Appl. No.: 87,866

[22] Filed: Jul. 9, 1993

[30] Foreign Application Priority Data

Jul. 23, 1992 [JP] Japan .................................. 4-196870
Apr. 16, 1993 [JP] Japan .................................. 5-089737

[51] Int. Cl.$^5$ ............................................ C07D 319/06
[52] U.S. Cl. ............................................ 549/335
[58] Field of Search ........................................ 549/335

[56] References Cited

U.S. PATENT DOCUMENTS

| | | | |
|---|---|---|---|
| 4,576,734 | 3/1986 | Ishii et al. | 252/404 |
| 4,739,080 | 4/1988 | Sasaki et al. | 549/335 |
| 4,769,479 | 9/1988 | Sasaki et al. | 549/335 |
| 4,845,244 | 7/1989 | Sasaki et al. | 549/335 |

FOREIGN PATENT DOCUMENTS 59-25826  2/1984 Japan .
59-231089 12/1984 Japan .

*Primary Examiner*—C. Warren Ivy
*Assistant Examiner*—A. A. Owens
*Attorney, Agent, or Firm*—Wenderoth, Lind & Ponack

[57] ABSTRACT

A hydroxyphenylpropionic ester represented by the formula of

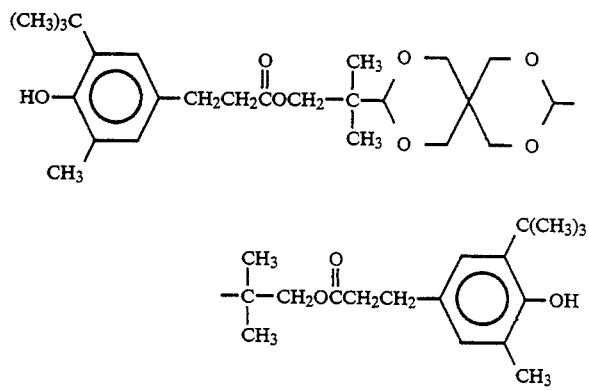

which has a crystal structure showing a sharp X-ray diffraction peak at a diffraction angle $2\theta = 7.9°$ by X-ray diffraction measurement using an X-ray of a Cu-K$_\alpha$ wavelength. This novel crystal exhibits largely advantageous effects in industrial production and usage of the ester because of its high purity, high quality, excellent filterability owing to the large crystal growth, and excellent fluidity owing to the large bulk specific gravity.

5 Claims, 5 Drawing Sheets

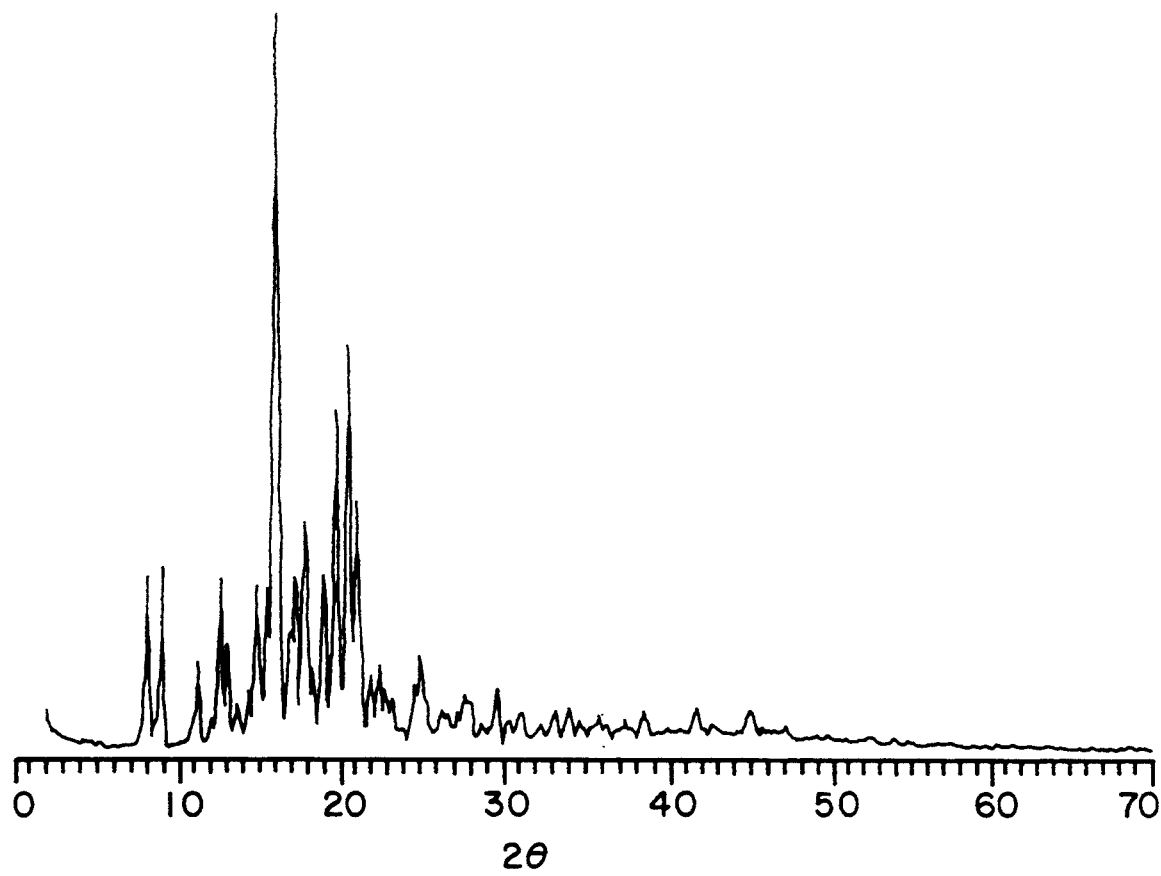
F I G. 1

HYDROXYPHENYLPROPIONIC ESTER HAVING NOVEL CRYSTAL STRUCTURE

The present invention relates to a hydroxyphenylpropionic ester having a novel crystal structure. The desired ester of the invention has a chemical name of 3,9-bis[2-{3-(3-t-butyl-4-hydroxy-5-methylphenyl)propionyloxy}-1,1-dimethylethyl]-2,4,8,10-tetraoxaspiro[5.5]undecane and is represented by the following formula (I):

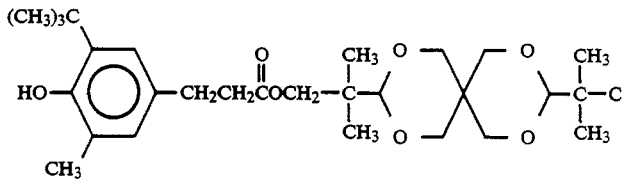 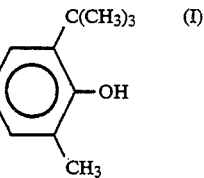

which will sometimes be referred to hereunder as a hydroxyphenylpropionic ester, or more simply as a compound of the formula (I).

The hydroxyphenylpropionic ester represented by the above formula (I) is known and described in Japanese Patent Publication No. 9,134/1991 (=Japanese Patent Kokai (Laid-Open) No. 25,826/1984), Japanese Patent Kokai (Laid-Open) No. 231,089/1984 and U.S. Pat. No. 4,576,734. The compound of the formula (I) can be useful as a stabilizer for preventing various kinds of synthetic resins—for example, polyolefins, such as polyethylene, polypropylene, etc., styrene series synthetic resins, such as polystyrene, high-impact polystyrene, ABS, etc., engineering plastics, such as polyacetal, polyamide, etc., and polyurethane—from deterioration, such as softening, embrittlement, surface cracking, discoloration, etc. caused by the action of heat, light and oxygen at the time of processing and use.

In general, the compound is produced by a transesterification between a lower alkyl ester of a corresponding hydroxyphenylpropionic acid and 3,9-bis(2-hydroxy-1,1-dimethylethyl)-2,4,8,10-tetraoxaspiro[5.5]undecane.

U.S. Pat. Nos. 4,739,080 and 4,769,479 disclose that the compound is polymorphic in crystal forms. Hitherto known crystal forms of the compound include the following:

(i) So-called γ-crystal, which is a glassy substance having a melting point of from about 45° C. to about 55° C. and can be obtained by the method described in U.S. Pat. No. 4,576,734.;

(ii) So-called αβ-crystal, which is in the form of white crystals having a melting point of from about 104° C. to about 109° C. and can be obtained by the method described in U.S. Pat. No. 4,739,080; and (iii) So-called δ-crystal, which is in the form of white crystals having a meltingpoint of from about 124° C. to about 127° C. and can be obtained by the method described in U.S. Pat. No. 4,769,479.

The γ-crystals can be obtained by melting a mixture comprising the ester (I) and impurities resulting from the production reaction, or by melting a product of the ester (I) of improved purity purified by means of column chromatography or the like, and then rapidly cooling the melt without using a solvent; and the melting point of the crystals is in the range of from about 45° C. to about 55° C. The Cu-K$_\alpha$ X-ray diffraction pattern of the γ-crystals is as shown in FIG. 5.

The αβ-crystals can be obtained by means of recrystallization from n-hexane, cyclohexane, or the like, and the melting point of the crystals is in the range of from about 104° C. to about 109° C. For example, in Japanese Patent Publication No. 9,134/1991 describes a purification process in which 3,9-bis[2-{3-(3,5-di-t-butyl-4-hydroxyphenyl)propionyloxy}-1,1-dimethylethyl]-2,4,8,10-tetraoxaspiro[5.5]undecane, which has a structure similar to that of the ester of the formula (I), is purified by means of recrystallization from n-hexane. When this purification process is strictly applied to the ester of the formula (I), there can be obtained αβ-crystals of the ester. The Cu-K$_\alpha$ X-ray diffraction pattern of the αβ-crystals is as shown in FIG. 4.

The δ-crystals can be obtained by allowing the hydroxyphenylpropionic ester of the formula (I) to deposit at 40° C. or above using, as a medium for recrystallization, an alicyclic hydrocarbon or a mixture of water and a water-soluble solvent, or by recrystallizing the ester from a mixture of a water-insoluble solvent and an aliphatic hydrocarbon; and the melting point of the crystals is in the range of from about 124° C. to about 127° C. The Cu-K$_\alpha$ X-ray diffraction pattern of the δ-crystals is as shown in FIG. 3.

Of the hitherto known crystals of the hydroxyphenylpropionic ester of the formula (I), the γ-crystals are in a glassy state, and the αβ-crystals and δ-crystals are in the form of fine powders. They all are not always satisfactory in terms of measurability, transportability, workability, etc. upon industrial production and handling since the crystals are poor in filterability and fluidity.

As a result of further studies, it has been found that, when recrystallized by using a particular combination of recrystallization solvents, the hydroxyphenylpropionic ester of the formula (I) forms a crystal having a crystal structure completely different from the prior ones, and that the hydroxyphenylpropionic ester having the novel crystal structure exhibits an improved filterability upon production, is greater in bulk specific gravity of final product and can be excellent in handling property, including fluidity.

Thus, the present invention provides a hydroxyphenylpropionic ester represented by the above formula (I) which has a crystal structure showing a sharp X-ray diffraction peak at a diffraction angle $2\theta = 7.9°$ by X-ray diffraction measurement using an X-ray of a Cu-K$_\alpha$ wavelength. This novel crystal structure according to the invention will be referred to as ε-crystal.

Next, the present invention will be explained with reference to the accompanying drawings, in which:

BRIEF DESCRIPTION OF DRAWINGS

FIG. 1 is an X-ray diffraction pattern of the desired compound having a crystal form of the invention (ε-crystal) and obtained in the later mentioned Example 1;

The ε-crystal of the hydroxyphenylpropionic ester represented by the formula (I) according to the invention, when subjected to an X-ray diffraction measurement using an X-ray of a Cu-K$_\alpha$ wavelength, gives an X-ray diffraction pattern as shown in FIG. 1. The detailed analysis of the X-ray diffraction pattern of FIG. 1 is shown in Table 1.

TABLE 1

Relative Strength at Each Diffraction Angle of ε-Crystal

| No. | Angle of Diffraction 2θ (degree) | Relative Strength (%) |
| --- | --- | --- |
| 1 | 7.90 | 23 |
| 2 | 8.80 | 24 |
| 3 | 10.90 | 12 |
| 4 | 11.90 | 4 |
| 5 | 12.45 | 23 |
| 6 | 12.85 | 16 |
| 7 | 13.44 | 7 |
| 8 | 14.15 | 9 |
| 9 | 14.60 | 23 |
| 10 | 15.32 | 23 |
| 11 | 15.92 | 100 |
| 12 | 17.00 | 24 |
| 13 | 17.67 | 32 |
| 14 | 18.13 | 12 |
| 15 | 18.85 | 25 |
| 16 | 19.57 | 48 |
| 17 | 20.40 | 59 |
| 18 | 20.89 | 37 |
| 19 | 21.77 | 12 |
| 20 | 22.36 | 13 |
| 21 | 22.75 | 9 |
| 22 | 23.16 | 8 |
| 23 | 24.80 | 14 |
| 24 | 26.21 | 6 |
| 25 | 26.54 | 6 |
| 26 | 27.11 | 5 |
| 27 | 27.52 | 8 |
| 28 | 28.55 | 4 |
| 29 | 29.51 | 10 |
| 30 | 30.98 | 6 |

The melting point of the ε-crystals according to the invention is in the range of from about 116° C. to about 119° C. when the purity of the crystals is quite high. However, the above melting point range may become a little lower, or it may become wider due to a deterioration in purity or to contamination of other forms of crystals, as often seen in other compounds. In general, it is roughly in the range of about 110° C. to about 124° C.

Figure 3:
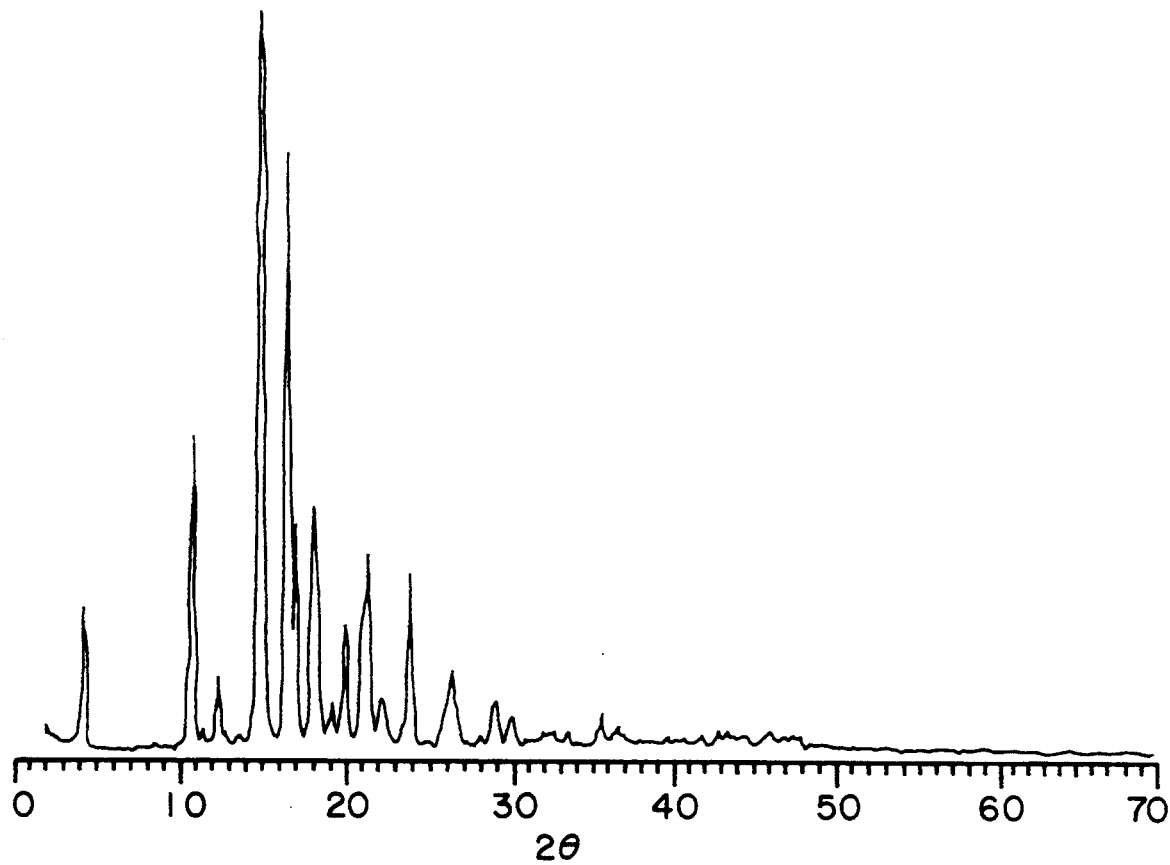
FIG. 3 is an X-ray diffraction pattern of the crystal (δ-crystal) obtained in the later mentioned Comparative Example 2.
Figure 4:
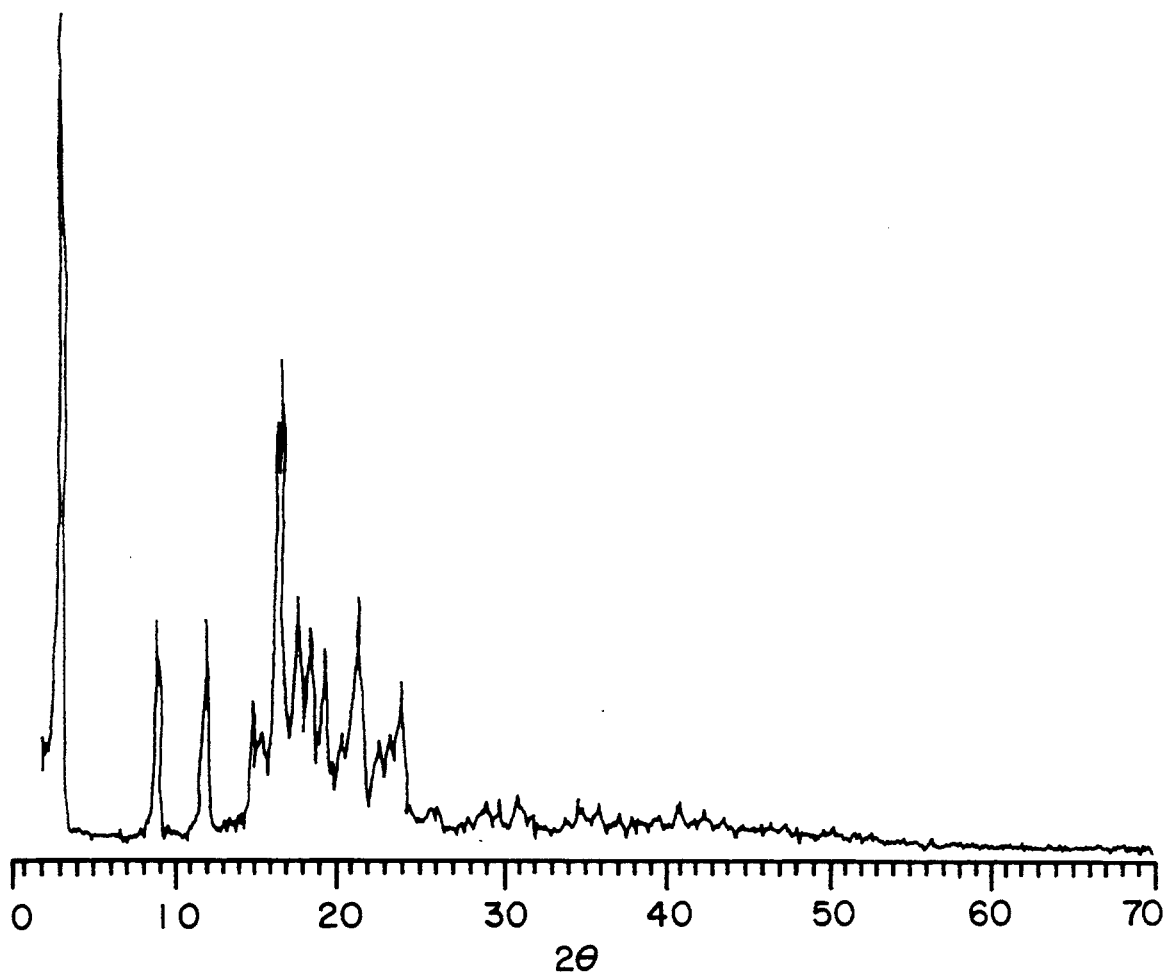
FIG. 4 is an X-ray diffraction pattern of the crystal (αβ-crystal) obtained in the later mentioned Comparative Example 3.
Figure 5:
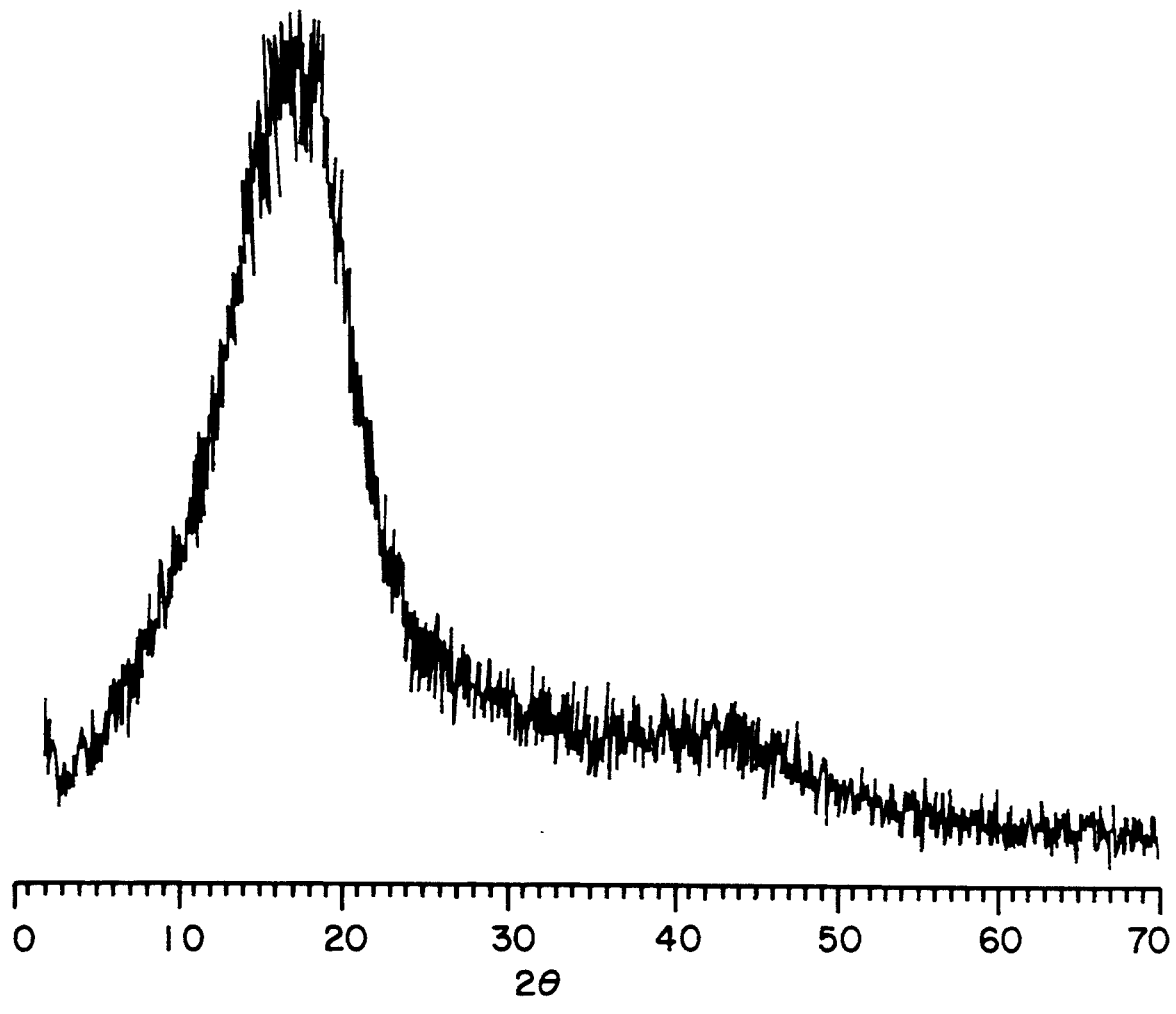
FIG. 5 is an X-ray diffraction pattern of the glass-like substance (ε-crystal) obtained in the later mentioned Reference Example 1.

The ε-crystals of the invention can be easily distinguished from the hitherto known δ-crystals, αβ-crystals and γ-crystals by X-ray diffraction measurement using an X-ray of a Cu-K$_\alpha$ wavelength, in particular, by the sharp peak at a diffraction angle 2θ=7.9°, as shown in Table 1 and FIG. 1. As is shown in FIG. 3 and described in U.S. Pat. No. 4,769,479, the X-ray diffraction pattern of δ-crystals shows sharp peaks at diffraction angles 2θ=4.2° and 2θ=10.6°. As is shown in FIG. 4 and described in U.S. Pat. No. 4,739,080, the αβ-crystals show sharp peaks at diffraction angles 2θ=2.8°, 2θ=8.7° and 2θ=11.7°. However, neither of the crystals shows a peak at a diffraction angle 2θ=7.9°. On the other hand, the γ-crystals show no characteristic diffraction peaks, as is shown in FIG. 5. The ε-crystals of the invention can be further differentiated from the δ-and αβ-crystals in that the former shows no diffraction peaks at around 2θ=3° to 4°, which are seen in the diffraction patterns of the δ- and αβ-crystals.

The ε-crystals of the invention grow faster, compared with the δ-crystals and the αβ-crystals. Consequently there can be obtained larger crystals, which have improved properties with respect to filterability upon production, as well as to transportability, measurability and workability upon handling of their products. Upon crystallizing operation the ε-crystals accompany impurities formed by the reaction in lesser quantities, and hence there can be obtained a product having a higher purity, compared with the cases of the δ-crystals and the αβ-crystals.

In addition, the ε-crystals can be obtained in a high yield since the crystals exhibit a lower solubility in organic solvents than the δ-crystals and the αβ-crystals, and also exhibit low compatibility with impurities formed by the reaction. Table 2 shows the solubility (measured at 20° C.) of the ε- and δ-crystals in various organic solvents.

TABLE 2

| Kind of Solvent | Solubility at 20° C. (g/100 g solvent) | |
| --- | --- | --- |
| | ε-Crystal | δ-Crystal |
| Methanol | 4 | 9 |
| Cyclohexane | 0.02 | 0.06 |
| Toluene | 9 | 15 |

Furthermore, the ε-crystals are smaller in hygroscopicity than the prior αβ- and δ-crystals. Consequently, the crystals can be used conveniently and advantageously with no additional treatment, such as re-drying and moisture-proof packing, even in such uses as the production of polyurethane, which is susceptible to the influence of moisture. Table 3 shows the results obtained when powdery products of ε-crystals and δ-crystals were exposed to an atmosphere of room temperature at a relative humidity of 100% for a predetermined period of time, and their moisture content was measured after the exposure according to the Karl Fischer method.

TABLE 3

| Exposure Period | Hygroscopicity (Water content in % by weight) | |
| --- | --- | --- |
| | ε-Crystal | δ-Crystal |
| 0 Days | 0.04 | 0.10 |
| 1 Day | 0.06 | 0.47 |
| 50 Days | 0.05 | 0.50 |
| 100 Days | 0.05 | 0.45 |

As described hereinabove, the ε-crystals of the invention possess a variety of excellent properties, which could never be expected from the prior arts.

The ε-crystals can be obtained by dissolving hydroxyphenylpropionic ester represented by the formula (I) into a mixture of a first solvent selected from aromatic hydrocarbons of 6 to 12 carbon atoms and a second solvent selected from aliphatic hydrocarbons of 6 to 10 carbon atoms, and then recrystallizing it with the addition of seed crystals. In this case, however, there may sometimes be formed a product mixed with other crystals, or a product inferior in purity, depending on crystallization conditions, such as the temperature of crystallization, the ratio of the first to second solvents, and the ratio of the solvent mixture to the hydroxyphenylpropionic acid. A high quality product can be obtained in a high yield by dissolving the hydroxyphenylpropionic ester represented by the formula (I) into a solvent mixture in which a third solvent selected from water-soluble organic solvents is further used in addition to the above-mentioned first and second solvents, and then crystallizing the ester by use of a seed crystal.

As examples of aromatic hydrocarbons of 6 to 12 carbon atoms used as the first solvent, mention may be made of benzene, toluene, ethylbenzene, xylene, cumene, cymene, chlorobenzene, and the like. Of these first solvents, toluene and xylene can be particularly preferred. As examples of aliphatic hydrocarbons of 6 to 10 carbon atoms used as the second solvent, mention may be made of n-hexane, n-heptane, n-octane, n-decane, and the like. Of these second solvents, n-hexane and n-heptane can be particularly preferred.

As examples of water-soluble organic solvents usable as the third solvent, mention may be made of alcohols, glycols, aliphatic ketones, aliphatic nitriles, alicyclic ethers, amides, tertiary amines, and the like. Of these solvents, alcohols can be particularly preferred. Examples of preferable alcohols include those containing 1 to 8 carbon atoms, for example, methanol, ethanol, n-propanol, isopropanol, n-butanol, isobutanol, n-hexanol, 2-ethylhexanol, and the like. Methanol can be particularly preferred. Examples of preferable glycols include those containing 2 to 6 carbon atoms, for example, ethylene glycol, trimethylene glycol, diethylene glycol, triethylene glycol, and the like. As examples of aliphatic ketones, mention may be made of acetone, methyl ethyl ketone, diethyl ketone, methyl isobutyl ketone, and the like. As examples of aliphatic nitriles, mention may be made of acetonitrile, propionitrile, and the like. As examples of alicyclic ethers, mention may be made of 1,4-dioxane, tetrahydrofuran, and the like. As examples of amides, mention may be made of N,N-dimethylformamide, N,N-dimethylacetamide, N-methyl-2-pyrrolidone, and the like. As examples of tertiary amines, mention may be made of triethylamine, pyridine, and the like.

Of the two or three kinds of solvents that constitute the mixed solvent, the first one (aromatic hydrocarbon) and the third one (water-soluble organic solvent) usually act as a solubilizer in the crystallization process of the hydroxyphenylpropionic ester represented by the formula (I), and could contribute to the improvement of purifying effects. The second solvent (aliphatic hydrocarbon) controls (a) the solubility of the hydroxyphenylpropionic ester in the first solvent and (b) the time required for the crystallization and could contribute to the improvement of yield. Since the third solvent (water-soluble organic solvent) is relatively poor in its compatibility with the second solvent, it is usually used together with the first and the second solvents. In ordinary cases, the third solvent (water-soluble organic solvent) is added, together with the second solvent, to the first solvent containing dissolved therein the hydroxyphenylpropionic ester. However, a mixture of the first and the third solvents may be prepared at first, and the hydroxyphenylpropionic ester may then be dissolved thereinto, followed by the addition of the second solvent.

In the crystallization operation, the first solvent is used preferably in an amount of from about 50% to about 150% by weight, based on the weight of the hydroxyphenylpropionic ester. The second solvent is used preferably in an amount of from about 0.8 to about 2.5 times by weight, based on the weight of the first solvent. If the solvents are used in quantities not falling within the above ranges, the results may be an undesirable lowering in the quality and yield of the desired product, or there may be formed other forms of crystals. Scaling to the crystallization apparatus may also result. In cases where the third solvent is used, it is preferred to use the third solvent in an amount of from about 0.2% to about 10% by weight, based on the weight of the first solvent. As a seed for the crystallization, $\epsilon$-crystal can be used with advantage. However, it is also possible to use $\delta$-crystal as the seed.

Usually, crystallization is carried out as follows: At first, a crude product of the hydroxyphenylpropionic ester represented by the formula (I)is completely dissolved into the first solvent at a temperature not higher than its boiling point. Then, the second solvent is added thereto, or the second solvent and the third solvent are added thereto, and crystallization is carried out at a temperature in the range of from 30° to 70° C. with addition of seed crystals which function as nuclei for the crystallization. Thereafter, the system is cooled to complete the crystallization. Alternatively, crystallization can be carried out by dissolving the crude product into a mixture of the first solvent and the second solvent, or into a mixture of the first solvent, the second solvent and the third solvent. The deposited crystals may be separated from the mother liquor by means, e.g., of filtration and then subjected to washing and drying to give isolated $\epsilon$-crystals.

In order to obtain $\epsilon$-crystals, the above crystallization operation must be conducted gradually. The form of crystals obtained is influenced by the quantity of the solvent mixture used and the ratio of the solvents contained therein, as well as by the crystallization temperature and the form of crystals used as a seed. When the crystallizing operation is conducted within a short period of time, $\delta$-crystals or a mixture of $\delta$- and $\epsilon$-crystals tends to be formed, and the crystals formed tend to be coagulated, causing deterioration in quality, including purity and hue of the desired product.

Thus, the $\epsilon$-crystals of the invention obtainable by using a particular combination of solvents can be excellent in crystal quality as well as in fluidity due to their high bulk specific gravity.

The present invention will be illustrated in further detail with reference to the following examples. The invention however is by no means limited by these examples. In the examples, all the percentages (%) are based on weight, unless otherwise specifically noted.

REFERENCE EXAMPLE 1

Into a 2 liter four-necked flask equipped with a stirrer, a thermometer and a fractionating column (number of theoretical stage=6) charged with Through-the-Packing were charged 863.4 g (3.45 mol) of methyl 3-(3-t-butyl-4-hydroxy-5-methylphenyl)propionate, 456.6 g (1.5 mol) of 3,9-bis(2-hydroxy-1,1-dimethylethyl)-2,4,8,10-tetraoxaspiro[5.5]undecane and 750 g of toluene. While stirring, the pressure was gradually reduced to 100 mmHg, and the temperature was raised. After it had been confirmed that 600 g of toluene had been distilled off into a receiver positioned at the upper part of the fractionating column and the toluene had returned from the receiver, the reaction mixture was heated under reflux for 1 hour at a temperature of about 90° C. and at a pressure of 100 mmHg. Subsequently, nitrogen gas was introduced into the system to allow its pressure to return to the atmospheric pressure, and then a solution of 3.45 g (0.15 mol) of lithium amide in 51.5 g of methanol was added at the atmospheric pressure. The temperature was gradually raised at the atmospheric pressure, and the reaction was completed by heating under reflux at 140° C. for 6 hours, while distilling off methanol formed by the reaction.

After completion of the reaction, a small quantity of toluene was added, and the reaction mixture was cooled to 85° C., neutralized with 12 g (0.2 mol) of acetic acid and washed with water. After the separation of the aqueous layer, the solvent was completely distilled off, to obtain 1,266 g of highly viscous, light yellow residue. In this distillation residue were contained, it was confirmed, 82.8% of 3,9-bis[2-{3-(3-t-butyl-4-hydroxy-5-methylphenyl)propionyloxy}-1,1-dimethylethyl]-2,4,8,10-tetraoxaspiro[5.5]undecane, 8.1% of methyl 3-(3-t-butyl-4-hydroxy-5-methylphenyl)propionate (starting material), and 9.1% of by-products. The highly viscous residue, when subjected to X-ray diffraction of Cu-K$_\alpha$ wavelength, gave an X-ray diffraction pattern as shown in FIG. 5.

EXAMPLE 1

In a reaction vessel equipped with a thermometer, a stirrer, a condenser and a dropping funnel, 200.0 g of the distillation residue obtained in Reference Example 1 was dissolved into 120.0 g of toluene at 80° C. Thereafter, 280.0 g of n-hexane was gradually added with stirring, and 1.0 g of seed of $\epsilon$-crystals was added at 50° C. Subsequently, the temperature of the resulting mixture was maintained in the range of from 50° to 55° C. for 7 hours to allow crystallization to proceed. The mixture was then gradually cooled to 20° C., and crystals obtained were collected by filtration at the same temperature and washed with n-hexane. The washed crystals were dried at 65° C. under reduced pressure, to obtain 164.1 g of white crystals having a melting point of 115° to 118° C.

Analysis of the white crystals showed that it contained 98.4% of desired 3,9-bis[2-{3-(3-t-butyl-4-hydroxy-5-methylphenyl)propionyloxy}-1,1-dimethylethyl]-2,4,8,10-tetraoxaspiro[5,5]undecane, 0.3% of methyl 3-(3-t-butyl-4-hydroxy-5-methylphenyl)propionate, and 1.3% of by-products. The white crystals, when subjected to X-ray diffraction of Cu-K$_\alpha$ wavelength, gave an X-ray diffraction pattern as shown in FIG. 1, in which a sharp X-ray diffraction peak was observed at a diffraction angle $2\theta = 7.9°$. Physical properties of the crystals are shown in Table 4.

EXAMPLE 2

In the same reaction vessel as the one used in Example 1, 200.0 g of the distillation residue obtained in Reference Example 1 was dissolved into 120.0 g of xylene at 80° C. Thereafter, 200.0 g of n-heptane and 2.0 g of methanol were gradually added with stirring, and 1.0 g of seed of $\epsilon$-crystals was added at 50° C. Subsequently, the temperature of the resulting mixture was maintained in the range of from 50° to 55° C. for 12 hours to allow crystallization to proceed. The mixture was then gradually cooled to 20° C., and crystals obtained were collected by filtration at the same temperature and washed with n-heptane. The washed crystals were dried at 65° C. under reduced pressure, to obtain 158.0 g of white crystals having a melting point of 115° to 118° C.

Analysis of the white crystals showed that it contained 98.5% of desired 3,9-bis[2-{3-(3-t-butyl-4-hydroxy-5-methylphenyl)propionyloxy}-1,1-dimethylethyl]-2,4,8,10-tetraoxaspiro[5.5]undecane, 0.3% of methyl 3-(3-t-butyl-4-hydroxy-5-methylphenyl)propionate, and 1.2% of by-products. The white crystals, when subjected to Cu-K$_\alpha$ X-ray diffraction measurement, gave an X-ray diffraction pattern which was similar to the one shown in FIG. 1 and in which was observed a sharp X-ray diffraction peak at a diffraction angle $2\theta = 7.9°$. Physical properties of the crystals are also shown in Table 4.

EXAMPLE 3

Into a mixture of 40.0 g of toluene and 1.0 g of methanol was dissolved at 65° C. 50.0 g of crystals obtained in Example 2. Subsequently, 60.0 g of n-hexane was gradually added with stirring, 0.25 g of seed of $\delta$-crystals was added at 50° C., and then the temperature of the resulting mixture was maintained in the range of from 50° to 55° C. for 12 hours. Thereafter, the resulting product was treated in the same manner as in Example 2, to obtain 47.2 g of white crystals having a melting point of 116° to 119° C. The white crystals, when subjected to X-ray diffraction of Cu-K$_\alpha$ wavelength, gave an X-ray diffraction pattern similar to the one shown in FIG. 1. Physical properties of the crystals and other experimental results are shown in Table 4.

COMPARATIVE EXAMPLE 1

Figure 2:
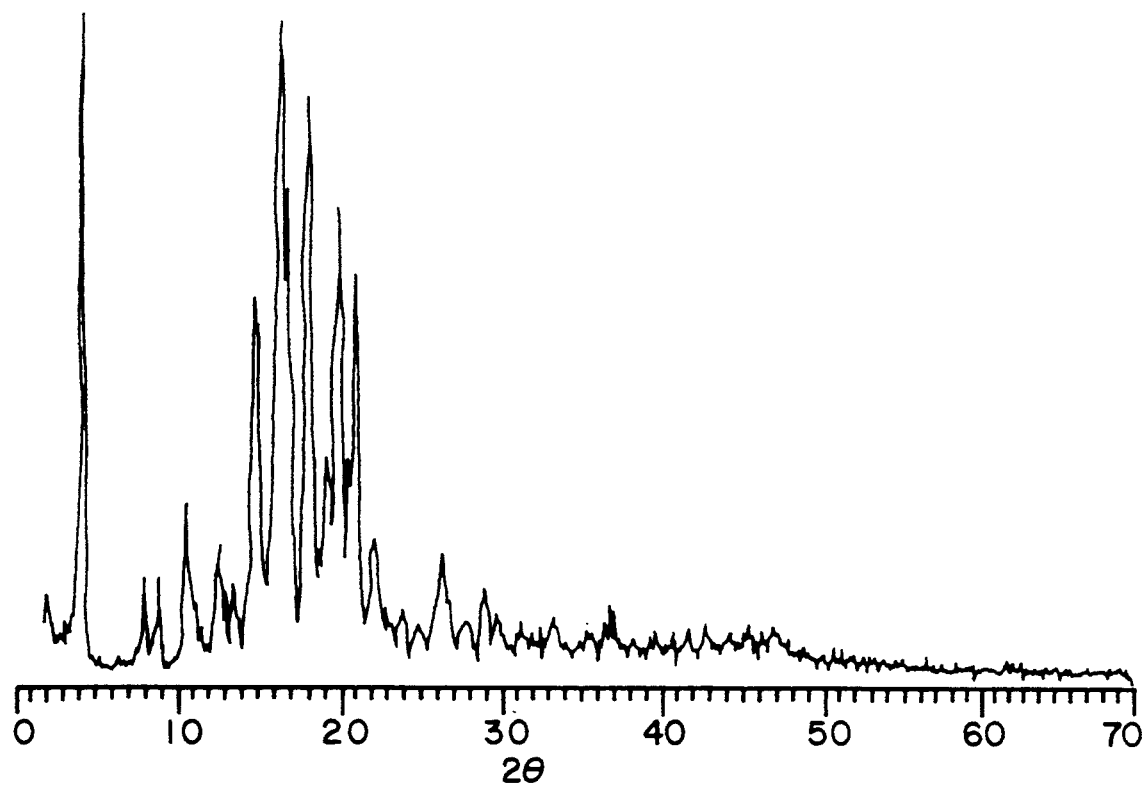
FIG. 2 is an X-ray diffraction pattern of the crystal (δε-crystal) obtained in the later mentioned Comparative Example 1.

The procedure of Example 1 was repeated, except that $\delta$-crystals were used as seed instead of $\epsilon$-crystals, to obtain 168.5 g of white crystals having a melting point of 121° to 124° C. The white crystals, when subjected to X-ray diffraction of Cu-K$_\alpha$ wavelength, gave an X-ray diffraction pattern as shown in FIG. 2. Physical properties of the crystals and other experimental results are shown in Table 5.

COMPARATIVE EXAMPLE 2

The procedure of Example 1 was repeated, except that 340.0 g of methanol was used in place of toluene and 60.0 g of water was used in place of n-hexane, to obtain 168.5 g of white crystals having a melting point of 124° to 127° C. The white crystals, when subjected to X-ray diffraction of Cu-K$_\alpha$ wavelength, gave an X-ray diffraction pattern as shown in FIG. 3. Physical properties of the crystals and other experimental results are shown in Table 5.

COMPARATIVE EXAMPLE 3

The procedure of Example 1 was repeated, except that 1,000 g of hexane alone was used in place of the mixture of toluene and n-hexane, the dissolving step was conducted at 70° C., the solution was cooled to 30° C., and the crystallization was conducted at the same temperature for 7 hours, to obtain 170.9 g of light yellow crystals having a melting point of 93° to 101° C. The crystals, when subjected to X-ray diffraction measurement of Cu-K$_\alpha$ wavelength, gave an X-ray diffraction pattern as shown in FIG. 4. Physical properties of the crystals and other experimental results are shown in Table 5.

TABLE 4

Results of Examples 1-3

| | Crystallizing Solvent | Form of Seed Crystal | Crystallizing Time (hrs) | Yield of Crystallization (%) | Crystal Form |
|---|---|---|---|---|---|
| Example 1 | Toluene/ n-Hexane | ε | 7 | 97.5 | ε |
| Example 2 | Xylene/ n-Heptane/ Methanol | ε | 12 | 94.4 | ε |
| Example 3 | Toluene/ n-Hexane/ Methanol | δ | 12 | 96.0 | ε |

| | Purity (%) | Appearance | Melting Point (°C.) | Bulk Specific Gravity (*) | Angle of Repose (°) | Angle of Spatula (°) |
|---|---|---|---|---|---|---|
| Example 1 | 98.4 | White | 115–118 | 0.59 | 45 | 57 |
| Example 2 | 98.5 | White | 115–118 | 0.60 | 45 | 58 |
| Example 3 | 99.5 | White | 116–119 | 0.66 | 47 | 58 |

[Note]
*Packed state

TABLE 5

Results of Comparative Examples 1-3

| | Crystallizing Solvent | Form of Seed Crystal | Crystallizing Time (hrs) | Yield of Crystallization (%) | Crystal Form |
|---|---|---|---|---|---|
| Comparative Example 1 | Toluene/ n-Hexane | δ | 7 | 97.5 | δε |
| Comparative Example 2 | Methanol/ Water | ε | 7 | 97.4 | δ |
| Comparative Example 3 | n-Hexane | ε | 7 | 96.0 | αβ |

| | Purity (%) | Appearance | Melting Point (°C.) | Bulk Specific Gravity (*) | Angle of Repose (°) | Angle of Spatula (°) |
|---|---|---|---|---|---|---|
| Comparative Example 1 | 95.8 | White | 121–124 | 0.43 | 50 | 65 |
| Comparative Example 2 | 97.4 | White | 124–127 | 0.40 | 53 | 74 |
| Comparative Example 3 | 93.0 | Light Yellow | 93–101 | — | — | — |

[Note]
*Packed state

The present invention provides the hydroxyphenyl propionic acid ester represented by the formula (I) having a novel hitherto unknown crystal structure (ε-crystal). The ε-crystals can be of high quality and can be highly useful for industrial uses since the crystals are not only large in size and can be excellent in filtering property upon production, but have a high bulk specific gravity and can be excellent in fluidity.

What is claimed is:

1. 3,9-Bis[2-{3-(3-t-butyl-4-hydroxy-5-methylphenyl)propionyloxy}-1,1-dimethylethyl]-2,4,8,10-tetraoxaspiro[5.5]undecane which has a crystal structure showing a sharp X-ray diffraction peak at a diffraction angle $2\theta = 7.9°$ by X-ray diffraction measurement using an X-ray of Cu-K$_\alpha$ wavelength.

2. 3,9-Bis[2-{3-(3-t-butyl-4-hydroxy-5-methylphenyl)propionyloxy}-1,1-dimethylethyl]-2,4,8,10-tetraoxaspiro[5.5]undecane according to claim 1, which has a melting point ranging from about 110° to about 124° C.

3. 3,9-Bis[2-{3-(3-t-butyl-4-hydroxy-5-methylphenyl)propionyloxy}-1,1-dimethylethyl]-2,4,8,10-tetraoxaspiro[5.5]undecane according to claim 2, which has a melting point ranging from about 116° to about 119° C.

4. 3,9-Bis[2-{3-(3-t-butyl-4-hydroxy-5-methylphenyl)propionyloxy}-1,1-dimethylethyl]-2,4,8,10-tetraoxaspiro[5.5]undecane according to claim 1, which shows no X-ray diffraction peak at a diffraction angle $2\theta$ of around 3° to 4°.

5. 3,9-Bis[2-{3-(3-t-butyl-4-hydroxy-5-methylphenyl)propionyloxy}-1,1-dimethylethyl]-2,4,8,10-tetraoxaspiro[5.5]undecane according to claim 1, which gives an X-ray diffraction pattern substantially the same as shown in FIG. 1.

* * * * *